United States Patent
Mautner et al.

(10) Patent No.: US 9,238,557 B2
(45) Date of Patent: Jan. 19, 2016

(54) CONVEYING OF FINE SOLIDS IN THE SYNTHESIS OF ALKYLCHLOROSILANES

(71) Applicant: WACKER CHEMIE AG, Munich (DE)

(72) Inventors: Konrad Mautner, Burghausen (DE); Jochen Gross, Tuessling (DE); Till Wuestenfeld, Riesa (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 14/281,939

(22) Filed: May 20, 2014

(65) Prior Publication Data

US 2014/0369771 A1 Dec. 18, 2014

(30) Foreign Application Priority Data

Jun. 13, 2013 (DE) .......................... 10 2013 211 067

(51) Int. Cl.

| C07F 7/12 | (2006.01) |
|---|---|
| B65G 53/16 | (2006.01) |
| B01J 8/18 | (2006.01) |
| C07F 7/16 | (2006.01) |
| B01J 8/28 | (2006.01) |
| B01J 8/00 | (2006.01) |

(52) U.S. Cl.
CPC .................. *B65G 53/16* (2013.01); *B01J 8/003* (2013.01); *B01J 8/1818* (2013.01); *B01J 8/1827* (2013.01); *B01J 8/1872* (2013.01); *B01J 8/28* (2013.01); *C07F 7/16* (2013.01)

(58) Field of Classification Search
USPC .................................. 556/451, 452, 466, 472
See application file for complete search history.

(56) References Cited

U.S. PATENT DOCUMENTS

| 2,389,931 | A | * | 11/1945 | Coe et al. ....................... 556/472 |
| 4,500,724 | A | | 2/1985 | Ward, III et al. |
| 5,512,662 | A | | 4/1996 | Kalchauer et al. |
| 5,783,721 | A | * | 7/1998 | Tsumura et al. .............. 556/472 |
| 2010/0150668 | A1 | | 6/2010 | Naunheimer et al. |
| 2010/0163465 | A1 | | 7/2010 | Bligh et al. |

FOREIGN PATENT DOCUMENTS

| DE | 10 2007 009 759 A1 | 8/2008 |
| EP | 0671402 A1 | 9/1995 |
| GB | 2 432 331 A | 5/2007 |
| JP | 60-78992 A | 5/1985 |
| JP | 9-194489 A | 7/1997 |
| WO | 0144253 A1 | 6/2001 |

OTHER PUBLICATIONS

Muschelknautz, E.; Wojahn, H., Chem.-Ing.-Technik, 46, 1974, p. 223-235 and English Abstract, Considered English abstract only.
W.Siegel, Pneumatische Foerderung, Vogel Buchverlag, Wuerzburg, 1991, p. 71-72 and English Abstract, Considered English abstract only.

* cited by examiner

*Primary Examiner* — Sudhakar Katakam
*Assistant Examiner* — Pancham Bakshi
(74) *Attorney, Agent, or Firm* — Brooks Kushman P.C.

(57) ABSTRACT

Pneumatic conveying of fine solids in the direct synthesis of alkylchlorosilanes conveying gas containing at least 50% by volume of alkyl chloride. The conveying apparatus preferably contains a means for switching conveying gas in the pneumatic conveying of fine solids.

10 Claims, 1 Drawing Sheet

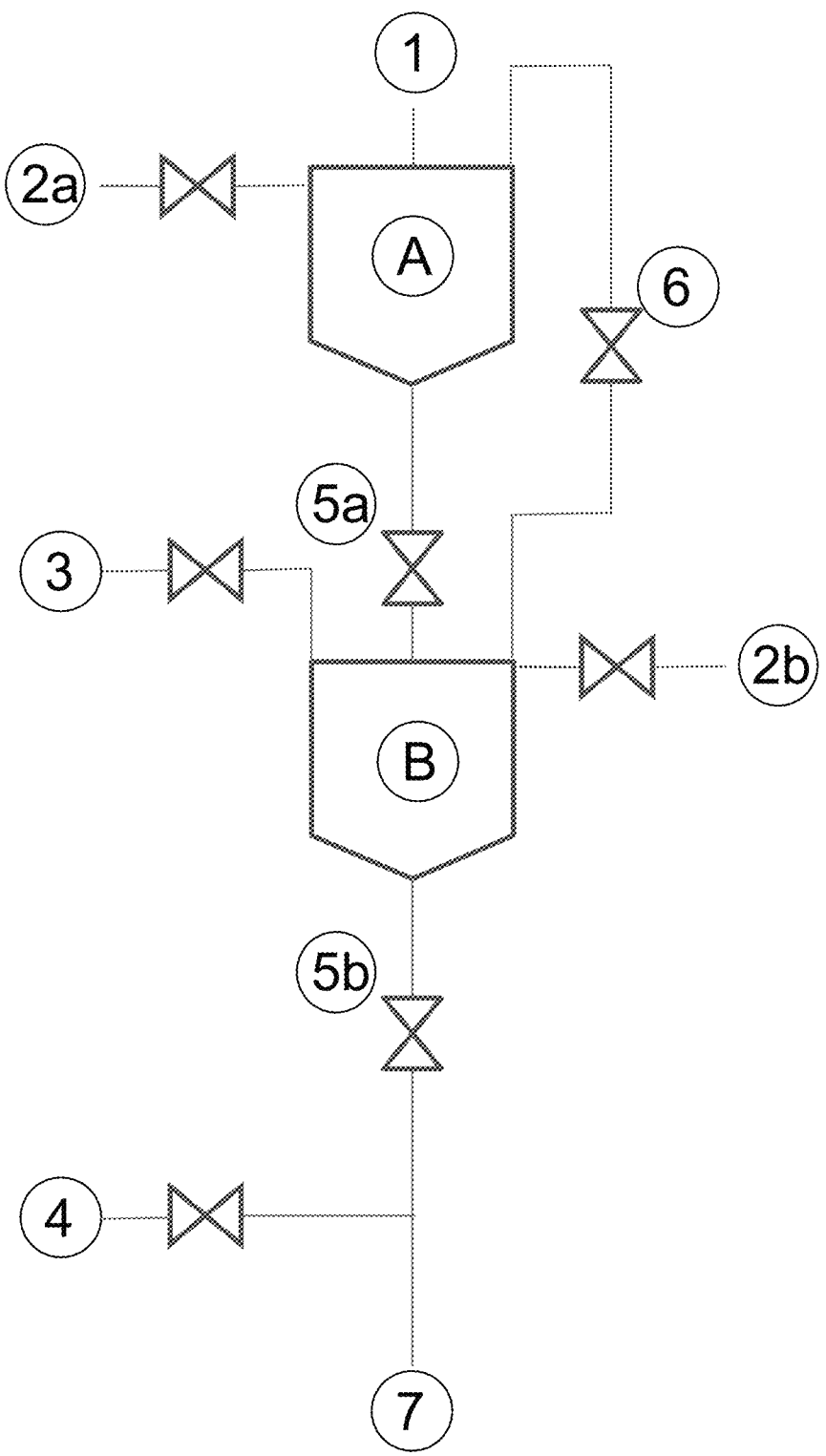

CONVEYING OF FINE SOLIDS IN THE SYNTHESIS OF ALKYLCHLOROSILANES

CROSS-REFERENCE TO RELATED APPLICATIONS

This application claims priority to German Patent Application No. 10 2013 211 067.7 filed Jun. 13, 2013 which is herein incorporated by reference.

BACKGROUND OF THE INVENTION

1. Field of the Invention

The invention relates to a method for pneumatic conveying of fine solids in the direct synthesis of alkylchlorosilanes, in which the conveying gas used is alkyl chloride, and to a method and apparatus for switching conveying gases in the pneumatic conveying of fine solids.

2. Background Art

The pneumatic conveying of solids, especially fine solids, has long been known (for example, Muschelknautz, E.; Wojahn, H., Chem.-Ing.-Technik, 46, 1974, 223-235) and is utilized whenever a high adaptation capacity of the conveying zones to the local circumstances is necessary, when environmentally friendly, closed conveying is necessary, and when a high flexibility of the distribution means, for example via pipe flow switches, is required. Another feature of pneumatic conveying is a low level of maintenance, and not least, pneumatic conveying offers the option of handling air-sensitive substances under a protective atmosphere.

For pneumatic conveying, gases such as air or nitrogen are typically used (see also W. Siegel, Pneumatische Förderung, Vogel Buchverlag, Würzburg, 1991, p. 71-72). Especially when combustible substances are involved, inert gases such as nitrogen or else argon are used.

In the direct synthesis of alkylchlorosilanes, fine solids or mixtures of solids are used, for example Si, catalysts or a mixture thereof, also referred to as catalyst composition. The reaction forms a spent catalyst composition which, as well as Si, includes distinctly elevated proportions of catalysts, promoters and secondary elements in the metallurgical silicon used. The direct synthesis of alkylchlorosilanes is described, for example, in EP 671402 A. Si grains, catalyst composition and spent catalyst composition are conveyed pneumatically in vessels and reactors in the alkylchlorosilane synthesis.

SUMMARY OF THE INVENTION

The invention provides a method for pneumatic conveying of fine solids in the direct synthesis of alkylchlorosilanes, in which the conveying gas used is a gas containing at least 50% by volume of alkyl chloride.

BRIEF DESCRIPTION OF THE DRAWINGS

FIG. 1 illustrates one embodiment of the claimed invention in schematic form.

DETAILED DESCRIPTION OF THE PREFERRED EMBODIMENT(S)

In the direct synthesis of alkylchlorosilanes, alkylchlorosilanes, silicon, Cu catalysts and promoters, e.g. Zn, Sn, Al and P, in elemental form or else in the form of compounds, are used. Preferably, a fluidized bed reactor is used. For conversion in a fluidized bed reactor, the raw materials used have to be fluidizable. According to the gas velocity of the reaction gas used, the particle size should therefore preferably average 1-500 µm, especially 2-200 µm. To maintain particular concentration profiles of the secondary elements, or of the catalysts or promoters, in continuously or quasi-continuously operated reactors, a substream is preferably drawn off continuously or discontinuously from the reactor. This can also be done together with the gaseous reaction product. In the startup of reactors, a spent catalyst composition is also obtained.

The pulverulent solids employed, especially silicon, Cu catalysts and promoters, have to be transported to the reactor, and the pulverulent solids remaining after the reaction have to be transported away from the reactor. This is preferably accomplished by pneumatic conveying. Since some of these are ignitable substances, air is not an option as a transport gas. Standard inert gases such as nitrogen or argon, being inert gases, dilute the alkyl chloride co-reactant, thus reducing the space-time yield, and lead to more offgas from the alkylchlorosilane synthesis.

According to the invention, these disadvantages can be avoided when the alkyl chloride reaction gas, preferably chloroethane in the synthesis of ethylchlorosilanes, especially chloromethane in the synthesis of methylchlorosilanes, is also used as the conveying gas. In this case, the alkyl chloride may contain secondary components in variable proportions, as may form in the direct synthesis, for example saturated and unsaturated hydrocarbons, other chlorohydrocarbons, hydrogen, hydrogen chloride and low-boiling silanes, especially when the conveying gas originates from recycling streams. It is also possible for inert gases selected from nitrogen and argon to be present up to 10% by volume. The alkyl chloride content in the conveying gas, however, is at least 50% by volume, preferably at least 85% by volume, and especially at least 95% by volume.

The conveying can be executed, for example, in the form of suspension flow conveying, stream flow conveying, dune flow conveying or else plug flow conveying. The gas velocity is preferably 5 m/s to 40 m/s, more preferably 5 to 20 m/s. The ratio of particle velocity to gas velocity is preferably 0.9 to 0.3, more preferably 0.9 to 0.5. The pressure drop is preferably 0.1 to 2.5 bar/100 m, more preferably 0.5 to 1.5 bar/100 m.

The pressure of the conveying gas used is preferably 1.5 to 10 bar abs. The temperature of the conveying gas used is typically ambient temperature, preferably 15 to 30° C., but is always such that the alkyl chloride constantly remains in gaseous form. The temperature of the solids conveyed preferably ranges from ambient temperature, preferably 15 to 30° C., up to the reaction temperature in the direct synthesis, typically 300° C.

In the direct synthesis of alkylchlorosilanes, preferably ethylchlorosilanes, especially methylchlorosilanes, are prepared, such as dimethyldichlorosilane, methyltrichlorosilane and trimethylchlorosilane. The especially preferred product is dimethyldichlorosilane.

The temperature in the direct synthesis is preferably at least 200° C., more preferably at least 250° C., and preferably at most 450° C., more preferably at most 400° C.

The pressure in the direct synthesis is preferably at least 1 bar, especially at least 1.5 bar and preferably at most 8 bar, especially at most 5 bar, reported in each case as absolute pressure.

Conveying gases in the pneumatic conveying are typically released to the atmosphere after dedusting. In the case of use of conveying gases containing at least 50% by volume of alkyl chloride, safe and environmentally friendly handling is especially preferred.

The invention further provides a method for switching conveying gas in pneumatic conveying of fine solids, which is illustrated by way of example in FIG. 1.

This is a method for switching conveying gas in the pneumatic conveying of fine solids, in which a mixture of fine solids and a first conveying gas (1) is introduced into a first vessel (A), a portion of the first conveying gas is removed (2a) in the vessel (A), the mixture of fine solids and the first conveying gas is discharged (5a) at the base of the vessel (A) into a second vessel (B) arranged beneath, in which the remainder of the first conveying gas is removed (2b) from the solids by purging with a purge gas (3), the mixture of purge gas and solids is discharged at the base of the vessel (B) and the mixture is pneumatically conveyed (7) with a second conveying gas (4).

With the method of the invention, it is possible to switch conveying gas for pneumatic conveying of fine solids in a simple and reliable manner. More particularly, environmentally friendly switching from an inert first conveying gas to combustible and/or environmentally harmful second conveying gases is possible.

The ventilation fitting (2a) ensures that either uncritical conveying gases are released to the atmosphere or environmentally critical conveying gases are released to a suitable point in the process or to an offgas cleaning plant.

In a preferred embodiment, the second conveying gas is the above-described gas containing at least 50% by volume of alkyl chloride. More particularly, the method for switching conveying gas is conducted before the method for pneumatic conveying of fine solids in the direct synthesis of alkylchlorosilanes, in which the conveying gas use is a gas containing at least 50% by volume of alkyl chloride.

While the solids can be treated in the vessel (B) after closing of the first fitting (5a), new solids can be introduced into the vessel (A) for a new method cycle.

The invention further provides an apparatus for switching conveying gas in the pneumatic conveying of fine solids, which is illustrated by way of example in FIG. 1.

This is an apparatus for switching conveying gas in the pneumatic conveying of fine solids, comprising a feed for fine solids (1) into a first vessel for fine solids (A), a ventilation fitting (2a) disposed in the vessel (A), a fitting (5a) disposed below the vessel (A), a vessel (B) disposed below the fitting (5a), a ventilation fitting (2b) disposed in the vessel (B), a purge gas fitting (3) disposed in the vessel (B), a fitting (5b) disposed below the vessel (B), a conveying gas fitting (4) disposed below the fitting (5b), and a line for removal of the pneumatically conveyed solids.

Preferably, a gas displacement system in the form of fitting (6) is disposed between vessels (A) and (B), and this can optionally serve to promote pressure equalization between vessels (A) and (B). The fittings (2a), (2b), (3), (4), (5a), (5b) and (6) are standard components for shutting off or regulating streams, preferably selected from shut-off valves, gates and other valves.

All the above symbols in the above formulae are each defined independently of one another. Unless stated otherwise, all pressures are 0.10 MPa (abs.) and all temperatures 20° C.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method for pneumatic conveying of fine solids in the direct synthesis of alkylchlorosilanes, comprising conveying particles into or out of a fluidized direct synthesis reactor by means of conveying gas containing at least 50% by volume of alkyl chloride, in which the gas velocity is 5 m/s to 40 m/s.

2. The method of claim 1, in which methylchlorosilanes are synthesized and the conveying gas used is a gas containing at least 50% by volume of methyl chloride.

3. The method of claim 1, in which the alkyl chloride content in the conveying gas is at least 85% by volume.

4. The method of claim 2, in which the alkyl chloride content in the conveying gas is at least 85% by volume.

5. The method of claim 1, in which a pressure drop during conveying is 0.1 to 2.5 bar/100 m.

6. A method for switching conveying gas in a pneumatic conveying of fine solids, comprising introducing a mixture of fine solids and a first conveying gas into a first vessel, removing a portion of the first conveying gas in the first vessel, discharging a mixture of fine solids and the first conveying gas at the base of the first vessel into a second vessel arranged beneath, and removing a remainder of the first conveying gas from the solids by purging with a purge gas, discharging the mixture of purge gas and solids at the base of the second vessel and pneumatically conveying the mixture with a second conveying gas.

7. The method of claim 6, in which the second conveying gas is a gas containing at least 50% by volume of alkyl chloride.

8. The method of claim 1, wherein at least a portion of alkyl chloride conveying gas is a recycle stream of alkyl chloride-containing gas.

9. The method of claim 1, wherein the particles are conveyed into a fluidized bed reactor for the synthesis of alkylchlorosilanes.

10. The method of claim 1, further comprising a method for switching conveying gas in a pneumatic conveying of fine solids, comprising introducing a mixture of fine solids and a first conveying gas into a first vessel, removing a portion of the first conveying gas in the first vessel, discharging a mixture of fine solids and the first conveying gas at the base of the first vessel into a second vessel arranged beneath, and removing a remainder of the first conveying gas from the solids by purging with a purge gas, discharging the mixture of purge gas and solids at the base of the second vessel and pneumatically conveying the mixture with a second conveying gas.

* * * * *